(12) United States Patent
Sakai et al.

(10) Patent No.: US 7,862,806 B2
(45) Date of Patent: Jan. 4, 2011

(54) HAIR COSMETIC COMPOSITION

(75) Inventors: Hirokazu Sakai, Tokyo (JP); Yoshimasa Okamoto, Tokyo (JP)

(73) Assignee: Kao Corporation, Tokyo (JP)

( * ) Notice: Subject to any disclaimer, the term of this patent is extended or adjusted under 35 U.S.C. 154(b) by 1334 days.

(21) Appl. No.: 10/825,430

(22) Filed: Apr. 16, 2004

(65) Prior Publication Data
US 2004/0258653 A1 Dec. 23, 2004

(30) Foreign Application Priority Data
Apr. 17, 2003 (JP) .............................. 2003-112270

(51) Int. Cl.
*A61Q 5/02* (2006.01)
(52) U.S. Cl. .................. 424/70.13; 424/70.1
(58) Field of Classification Search ........................ None
See application file for complete search history.

(56) References Cited

U.S. PATENT DOCUMENTS

| | | | |
|---|---|---|---|
| 5,656,668 A | | 8/1997 | Motion et al. |
| 5,661,118 A | | 8/1997 | Cauwet et al. |
| 5,876,705 A | * | 3/1999 | Uchiyama et al. ......... 424/70.12 |
| 6,060,612 A | | 5/2000 | Hong et al. |
| 6,162,423 A | | 12/2000 | Sebag et al. |
| 2002/0010215 A1 | | 1/2002 | Shiroyama et al. |
| 2003/0082132 A1 | | 5/2003 | Ogoh |
| 2004/0156815 A1 | * | 8/2004 | Sakai et al. ............... 424/70.21 |
| 2004/0157984 A1 | * | 8/2004 | Sakai et al. .................. 524/588 |

FOREIGN PATENT DOCUMENTS

| | | |
|---|---|---|
| EP | 0 278 505 A2 | 8/1988 |
| EP | 1 061 121 A1 | 12/2000 |
| EP | 1 090 623 A1 | 4/2001 |
| EP | 1 166 766 A1 | 1/2002 |
| EP | 1 433 466 A2 | 6/2004 |
| JP | 8-59443 | 3/1996 |
| JP | 2002-338459 | 11/2002 |
| JP | 2003-12474 | 1/2003 |
| WO | WO 96/23479 | 8/1996 |
| WO | WO 00/25735 | 5/2000 |

OTHER PUBLICATIONS

XP-002295514 "cleansing and conditioning of hair", pp. 65-69 (1998).*
WO 96/23479, Abstract (Aug. 8, 1996).
JP 2003-12474, Abstract (Jan. 15, 2003).
JP 2002-338459, Abstract (Nov. 27, 2002).
Chemical Abstracts Service, Database Accession No. 135: 348708, XP-002329472, JP 2001-302465, Oct. 31, 2001.

* cited by examiner

*Primary Examiner*—Jyothsna A Venkat
(74) *Attorney, Agent, or Firm*—Oblon, Spivak, McClelland, Maier & Neustadt, L.L.P.

(57) ABSTRACT

Provided is a hair cosmetic composition containing (A) from 0.001 to 10 wt. % of an amphipathic amide lipid, and (B): from 0.05 to 10 wt. % of a dialkyl ether or ethylene glycol dialkyl ether with an alkyl group having from 18 to 22 carbon atoms, or an ethylene glycol monofatty acid ester, ethylene glycol difatty acid ester, fatty acid monoethanolamide or acylated β-alanine with an acyl group having from 18 to 22 carbon atoms.

The hair cosmetic composition of the present invention for example, protects the hair from physical or chemical stimulation, prevents appearance of split ends and broken hair, imparts natural smoothness, moist feeling, resilience and strength, and moisture retention property to the hair after treatment (shampooing), and at the same time has excellent storage stability.

7 Claims, No Drawings

HAIR COSMETIC COMPOSITION

FIELD OF THE INVENTION

The present invention relates to hair cosmetic compositions capable of for example, imparting hair with a pleasant feel and at the same time, suppressing generation of split ends and broken hair.

BACKGROUND OF THE INVENTION

Since hair is always exposed to physical stimulation by daily hair care routines such as heat drying with a hair dryer and brushing, and chemical stimulation by shampooing, permanent weaving, dyeing and bleaching, it is often in a damaged state with a partial component or structural loss. A change in hair quality due to aging accelerates this damage and also causes the loss of resilience and strength to hair.

It is a common practice to protect or repair hair in a damaged state by making up for the lost component or structure or analogue thereof. Interaction (affinity) between a protecting base and hair is considered important for the exhibition of a protecting or restoring function, and a method of using a sphingolipid or protein derivative as a protecting base has been used widely as a useful technique. For example, a hair shampoo agent containing a surfactant made of an anionic surfactant and a bipolar ionic surfactant, cationic polymer, and ceramide or glycosylceramide has been proposed (Japanese Patent Application Laid-Open No. Hei 8-59443). The agent however cannot contain an adequate amount of a protecting base such as a ceramide or glycosylceramide because it has a high melting point and easily crystallizes. Moreover, even this protecting base added in a slight amount does not readily penetrate into the hair. There is a continuing desire to improve the amount of protecting base penetrating into the hair. The conventional hair cosmetic composition is therefore accompanied with the problem that the protecting base incorporated therein cannot function well.

SUMMARY OF THE INVENTION

In the present invention, there is thus provided a hair cosmetic composition containing the following components (A) and (B):

(A): from 0.001 to 10 wt. % of an amphipathic amide lipid, and (B): from 0.05 to 10 wt. % of at least one compound selected from dialkyl ethers with an alkyl group having from 18 to 22 carbon atoms, ethylene glycol dialkyl ethers with an alkyl group having from 18 to 22 carbon atoms, ethylene glycol monofatty acid esters with an acyl group having from 18 to 22 carbon atoms, ethylene glycol difatty acid esters with an acyl group having from 18 to 22 carbon atoms, fatty acid monoethanolamides with an acyl group having from 18 to 22 carbon atoms, and acylated β-alanines with an acyl group having from 18 to 22 carbon atoms.

DETAILED DESCRIPTION OF THE INVENTION

The present invention relates to a hair cosmetic composition capable of having many benefits including for example, causing a protecting base incorporated therein to adsorb to hair sufficiently and thereby protecting the hair from physical and chemical stimulations to prevent appearance of split ends or broken hair, imparting the hair, after treatment (shampooing), with natural smoothness, moist feeling, resilience and strength, and moisture retention property, and having excellent storage stability.

The present inventors have found that incorporation of a compound serving as a pearling agent together with an amphipathic amide lipid serving as a protecting base in a hair cosmetic composition improves the dispersion stability of the amphipathic amide lipid and heightens adsorption of it to the hair to improve the hair protecting effect and at the same time, imparts a pleasant feel to hair significantly.

The amphipathic amide lipid as Component (A) preferably has 1 or 2 amide groups; preferably has, as a carbon chain bonded to the carbonyl group of the amide group, a $C_{5-60}$ alkyl or alkylene group which may be substituted with a hydroxy group and may contain an ester bond in its main chain; and preferably contains 1 to 5 hydroxy or $C_{1-30}$ alkoxy groups in total. The following compounds (A-1) to (A-4) are specific examples of the amphipathic amide lipid.

(A-1) Diamide compounds represented by formula (1):

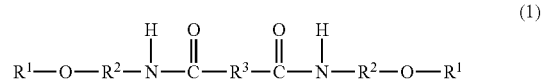

wherein, $R^1$ represents a linear or branched $C_{1-12}$ hydrocarbon group which may be substituted with a hydroxy group(s) and/or alkoxy group(s), $R^2$ represents a linear or branched divalent $C_{1-5}$ hydrocarbon group and $R^3$ represents a linear or branched divalent $C_{1-22}$ hydrocarbon group.

As $R^1$ in formula (1), linear or branched $C_{1-12}$ alkyl groups which may be substituted with 1 to 3 groups selected from a hydroxy group and $C_{1-6}$ alkoxy groups are preferred. Of these, unsubstituted $C_{1-12}$ alkyl groups and $C_{2-12}$ alkyl groups substituted with 1 to 2 hydroxy groups and one $C_{1-6}$ alkoxy group or with one hydroxy group and one $C_{1-6}$ alkoxy group are more preferred. Specific examples include methyl, ethyl, propyl, butyl, hexyl, dodecyl, 2-methylpropyl, 2-ethylhexyl, 2-hydroxyethyl, 9-hydroxynonyl, 2,3-dihydroxypropyl, 2-methoxyethyl, 2-hydroxy-3-methoxypropyl and 9-methoxynonyl groups, of which 2-hydroxyethyl, methyl, dodecyl and 2-methoxyethyl groups are preferred.

As $R^2$ in formula (1), linear or branched $C_{2-5}$ alkylene groups are preferred, and linear or branched $C_{2-3}$ alkylene groups are preferred. Specific examples include ethylene, trimethylene, tetramethylene, pentamethylene, 1-methylethylene, 2-methylethylene, 1-methyltrimethylene, 2-methyltrimethylene, 1,1-dimethylethylene and 2-ethyltrimethylene groups. Of these, ethylene and trimethylene groups are preferred.

As $R^3$ in formula (1), linear or branched divalent $C_{2-22}$ hydrocarbon groups are preferred, and linear or branched $C_{11-22}$ alkylene groups and alkenylene groups having 1 to 4 double bonds are more preferred. Specific examples include ethylene, trimethylene, tetramethylene, hexamethylene, heptamethylene, octamethylene, decamethylene, undecamethylene, dodecamethylene, tridecamethylene, tetradecamethylene, hexadecamethylene, octadecamethylene, 1-methylethylene, 2-ethyltrimethylene, 1-methylheptamethylene, 2-methylheptamethylene, 1-butylhexamethylene, 2-methyl-5-ethylheptamethylene, 2,3,6-trimethylheptamethylene, 6-ethyldecamethylene, 7-methyltetradecamethylene, 7-ethylhexadecamethylene, 7,12-dimethyloctadecamethylene, 8,11-dimethyloctadecamethylene, 7,10-dimethyl-7-ethylhexadecamethylene, 1-octadecylethylene, ethenylene, 1-octadecenylethylene, 7,11-octadecadienylene, 7-ethenyl-9-hexadecamethylene, 7,12-dimethyl-7,11-octadecadienylene and 8,11-dimethyl-7,11-octadecadienylene groups. Of these, 7,12-dimethyloctadecamethylene, 7,12-dimethyl-7,11-octadecadienylene, octadecamethylene, undecamethylene and tridecamethylene groups are preferred.

Preferred diamide compounds (1) are compounds having the above-described preferred groups as $R^1$, $R^2$ and $R^3$, respectively. Specific examples are the following compounds:

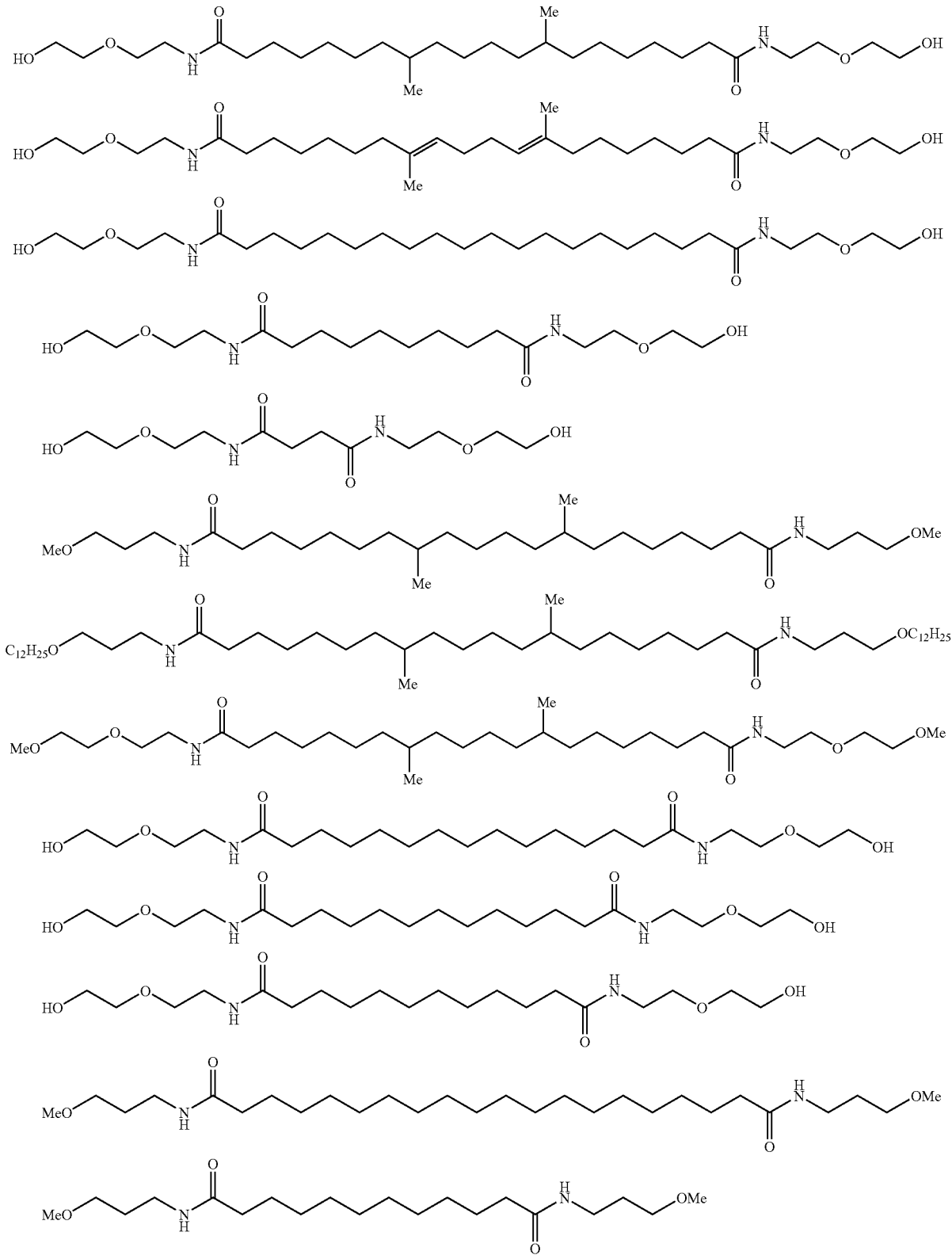

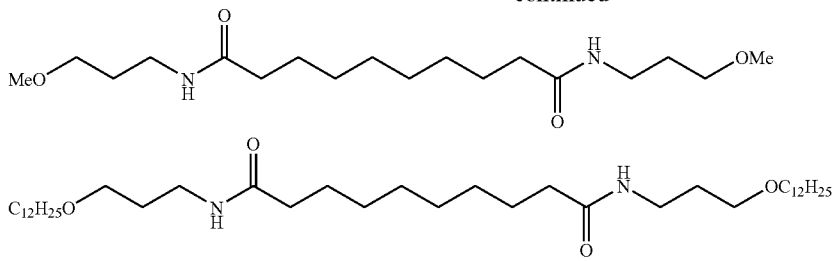

(A-2) Ceramides represented by the following formula (2):

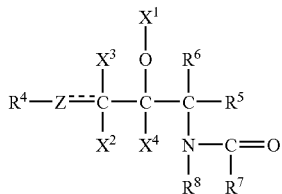
(2)

wherein, $R^4$ represents a linear, branched or cyclic, saturated or unsaturated $C_{4-30}$ hydrocarbon group which may be substituted with hydroxy, oxo or amino group(s), Z represents a methylene group, a methine group or an oxygen atom, a broken line represents the presence or absence of a π bond, $X^1$ represents a hydrogen atom, an acetyl group or a glyceryl group, or, together with the adjacent oxygen atom, forms an oxo group, $X^2$, $X^3$ and $X^4$ each independently represents a hydrogen atom, a hydroxy group or an acetoxy group (with the proviso that when Z represents a methine group, one of $X^2$ and $X^3$ represents a hydrogen atom and the other does not exist, and when —O—$X^1$ represents an oxo group, $X^4$ does not exist), $R^5$ and $R^6$ each independently represents a hydrogen atom, a hydroxy group, a hydroxymethyl group or an acetoxymethyl group, $R^7$ represents a linear, branched or cyclic, saturated $C_{5-35}$ hydrocarbon group which may be substituted with a hydroxy or amino group, or the saturated $C_{5-35}$ hydrocarbon group in which a linear, branched or cyclic, saturated or unsaturated $C_{8-22}$ fatty acid which may be substituted with hydroxy group(s) is ester-bonded at the ω-position of the hydrocarbon group, and $R^8$ represents a hydrogen atom or a linear or branched, saturated or unsaturated hydrocarbon group which may have substituent(s) selected from a hydroxy group, hydroxyalkoxy groups, alkoxy groups and an acetoxy group, and has 1 to 8 carbon atoms in total.

As $R^4$ in formula (2), linear, branched or cyclic, saturated or unsaturated $C_{7-22}$ hydrocarbon groups which may be substituted with hydroxy group(s) are preferred. As $X^1$, a hydrogen atom and a glyceryl group are preferred. It is preferred that none or one of $X^2$, $X^3$, and $X^4$ represents a hydroxy group and the others represent a hydrogen atom. It is preferred that one of $R^5$ and $R^6$ represents a hydrogen atom or a hydroxymethyl group and the other represents a hydrogen atom. In $R^7$, preferred examples of the fatty acid which may be ester-bonded or amide-bonded to the saturated hydrocarbon group at the ω-position thereof include isostearic acid, 12-hydroxystearic acid and linoleic acid. As $R^8$, a hydrogen atom and hydrocarbon groups which may be substituted with 1 to 3 substituents selected from a hydroxy group, hydroxyalkoxy groups and alkoxy groups and have 1 to 8 carbon atoms in total are preferred.

As ceramide (2), preferred are the following compounds (2a) and (2b).

(A-2a) Natural ceramides or natural type ceramides represented by formula (2a), and derivatives thereof (which will hereinafter be called "natural type ceramides")

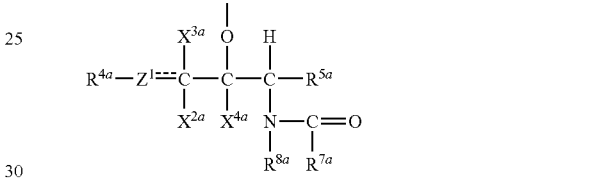
(2a)

wherein, $R^{4a}$ represents a linear, branched or cyclic, saturated or unsaturated $C_{7-19}$ hydrocarbon group which may be substituted with a hydroxy group, $Z^1$ represents a methylene or methine group, a broken line represents the presence or absence of a π bond, $X^{1a}$ represents a hydrogen atom or, together with the adjacent oxygen atom, forms an oxo group, $X^{2a}$, $X^{3a}$ and $X^{4a}$ each independently represents a hydrogen atom, a hydroxy group or an acetoxy group (with the proviso that when $Z^1$ represents a methine group, one of $X^{2a}$ and $X^{3a}$ represents a hydrogen atom and the other does not exist, and when —O—$X^{1a}$ represents an oxo group, $X^{4a}$ does not exist), $R^{5a}$ represents a hydroxymethyl group or an acetoxymethyl group, $R^{7a}$ represents a linear, branched or cyclic, saturated $C_{5-30}$ hydrocarbon group which may be substituted with hydroxy group(s), or the saturated $C_{5-30}$ hydrocarbon group in which a linear or branched, saturated or unsaturated $C_{8-22}$ fatty acid which may be substituted with hydroxy group(s) is ester-bonded at the ω-position of the hydrocarbon group, and $R^{8a}$ represents a hydrogen atom or a $C_{1-4}$ alkyl group.

Preferred are compounds in which $R^{4a}$ is a linear $C_{7-19}$, more preferably $C_{13-15}$ alkyl group, $Z^1$ is a methine group, one of $X^{2a}$ and $X^{3a}$ is a hydrogen atom, and $R^{7a}$ is a linear $C_{9-27}$ alkyl group which may be substituted with hydroxy group(s). In addition, $X^{1a}$ preferably represents a hydrogen atom or, together with an oxygen atom, forms an oxo group. More preferred examples of $R^{7a}$ include a tricosyl group, a 1-hydroxypentadecyl group, a 1-hydroxytricosyl group, a heptadecyl group, a 1-hydroxyundecyl group and a nonacosyl group having a linoleic acid ester-bonded at the ω-position of the group.

Specific examples of the natural type ceramides include Ceramide Types 1 to 7 having the below-described structures and obtained by amidation of sphingosine, dihydrosphingosine, phytosphingosine or sphingadienine (for example, FIG. 2 of J. Lipid Res., 24, 759(1983), and pig and human ceramides as described in FIG. 4 of J. Lipid Res., 35, 2069 (1994)).

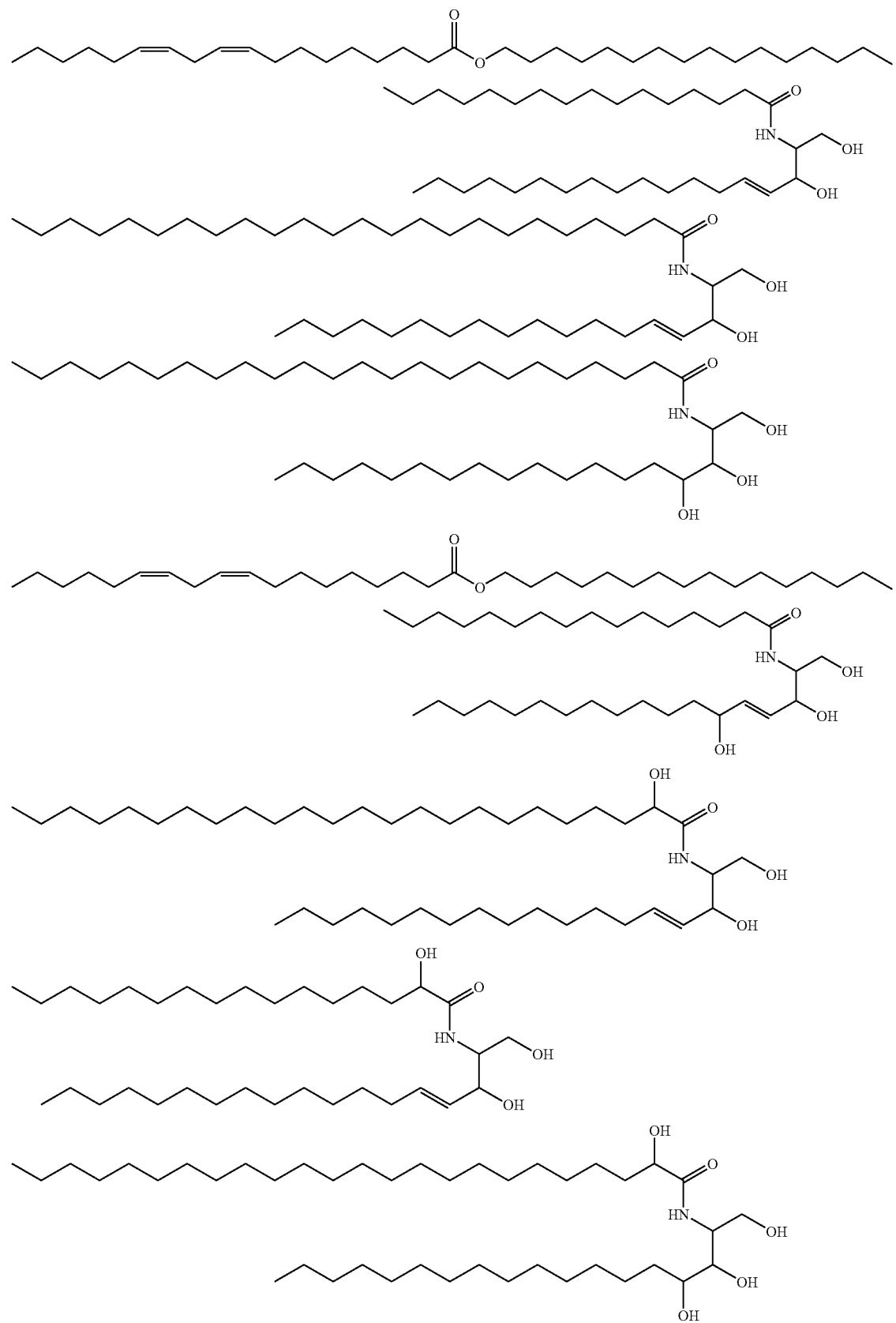

-continued

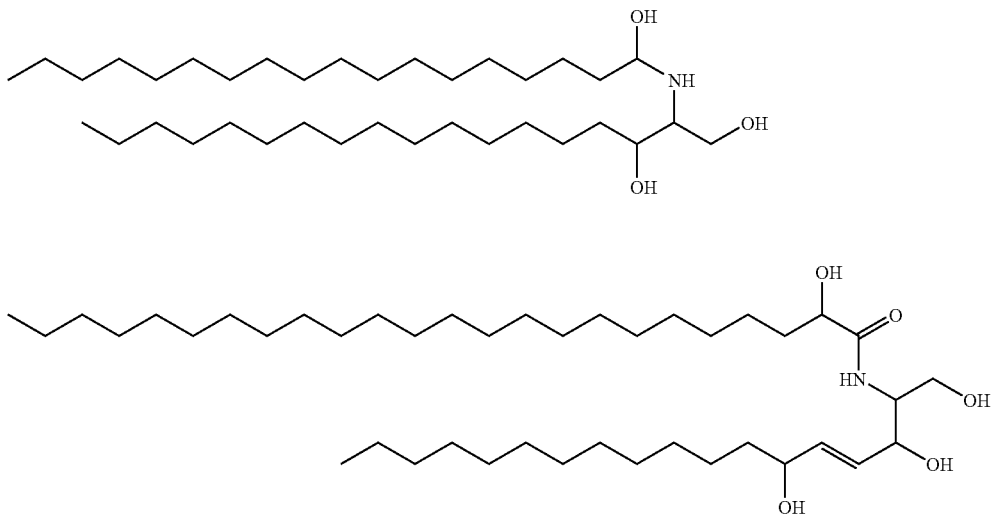

Examples also include N-alkyl derivatives (for example, N-methyl derivatives) of the above-described ceramides. They may be either a natural extract or synthesized product. Commercially available ones are also usable.

(A-2b) Pseudo type ceramides represented by the following formula (2b):

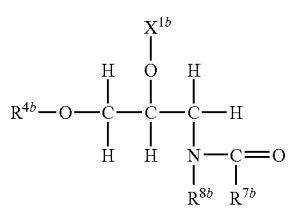

(2b)

wherein, $R^{4b}$ represents a linear, branched or cyclic, saturated or unsaturated $C_{10-22}$ hydrocarbon group which may be substituted with hydroxy group(s), $X^{1b}$ represents a hydrogen atom, an acetyl group or a glyceryl group, $R^{7b}$ represents a linear, branched or cyclic, saturated or unsaturated $C_{5-22}$ hydrocarbon group which may be substituted with hydroxy or amino group(s), or the hydrocarbon group in which a linear or branched, saturated or unsaturated $C_{8-22}$ fatty acid which may be substituted with hydroxy group(s) is ester-bonded at the ω-position of the hydrocarbon group, and $R^{8b}$ represents a hydrogen atom or an alkyl group which may be substituted with hydroxy group(s), hydroxyalkoxy group(s), alkoxy group(s) or acetoxy group(s) and has 1 to 8 carbon atoms in total.

Preferred as $R^{7b}$ are a nonyl group, a tridecyl group, a pentadecyl group, an undecyl group having linoleic acid ester-bonded at the ω-position of the group, a pentadecyl group having linoleic acid ester-bonded at the ω-position of the group, a pentadecyl group having 12-hydroxystearic acid ester-bonded at the ω-position of the group, and an undecyl group having methyl-branched isostearic acid amide-bonded at the ω-position of the group. As the hydroxyalkoxy or alkoxy groups for $R^{8b}$, preferred are those having 1 to 8 carbon atoms.

As the pseudo type ceramides (2b), those having as $R^{4b}$ a hexadecyl group, as $X^{1b}$ a hydrogen atom, as $R^{7b}$ a pentadecyl group, and as $R^{8b}$ a hydroxyethyl group; those having as $R^{4b}$ a hexadecyl group, as $X^{1b}$ a hydrogen atom, as $R^{7b}$ a nonyl group, and as $R^{8b}$ a hydroxyethyl group; or those having as $R^{1b}$ a hexadecyl group, as $X^{1b}$ a glyceryl group, as $R^{7b}$ a tridecyl group, and as $R^{8b}$ a 3-methoxypropyl group are preferred, with those having as $R^{4b}$ a hexadecyl group, as $X^{1b}$ a hydrogen atom, as $R^{7b}$ a pentadecyl group, and as $R^{8b}$ a hydroxyethyl group being more preferred. Specific preferred examples include those represented by the following formulas:

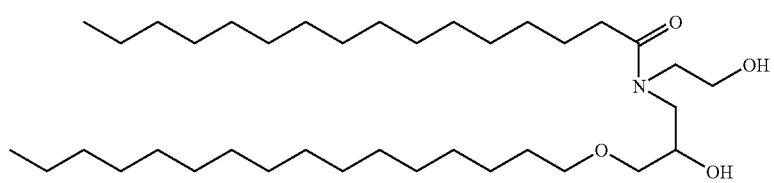

-continued

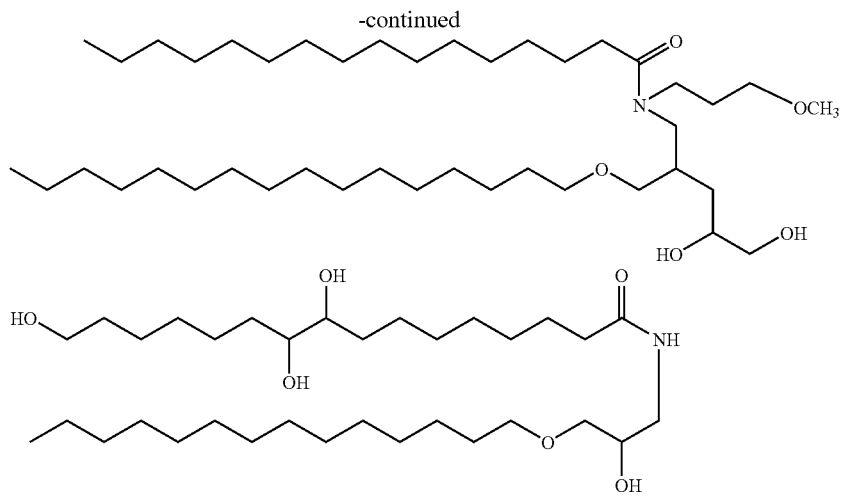

(A-3) Diamide compounds represented by the following formula (3):

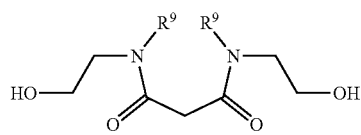                                      (3)

wherein, $R^9$ represents a $C_{10-18}$ alkyl group which may be substituted with hydroxy group(s).

Specific examples of compound (3) include the compound represented by the following formula:

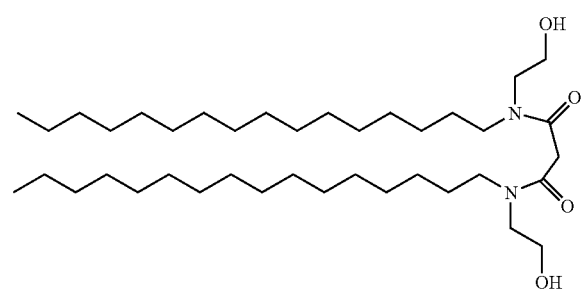

(A-4) Amide compounds represented by the following formula (4):

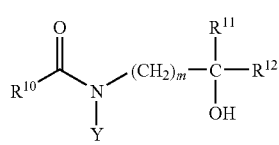                                      (4)

wherein, $R^{10}$ represents a linear or branched, saturated or unsaturated $C_{9-31}$ hydrocarbon group which may be substituted with hydroxy group(s), or a 2-dodecen-1-yl succinic acid residue, m stands for an integer of from 1 to 3, $R^{11}$ and $R^{12}$ each represents a hydrogen atom or a $C_{1-4}$ alkyl or hydroxyalkyl group, Y represents a linear or branched, saturated or unsaturated $C_{10-32}$ hydrocarbon group which may be substituted with hydroxy group(s), or a substituent represented by the following formula:

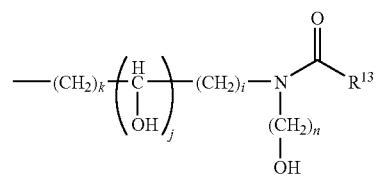

in which, k, i and n each stands for an integer of from 1 to 3, j stands for 0 or 1, and $R^{13}$ represents a linear or branched, saturated or unsaturated $C_{9-31}$ hydrocarbon group which may be substituted with hydroxy group(s).

Specific examples of Compound (4) include a compound represented by the following formula:

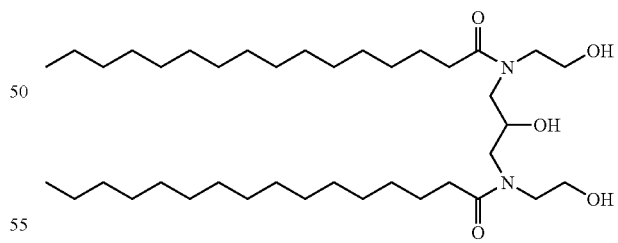

Of the above-described amphipathic amide lipids, those represented by formula (1) or (2b) are preferred, and those represented by formula (1) are more preferred.

As Component (A), two or more of these amphipathic amide lipids may be used in combination. Its (their) content in the hair cosmetic composition of the present invention is preferably from 0.001 to 10 wt. %, more preferably from 0.1 to 5 wt. %, even more preferably from 0.5 to 1 wt. % in view of imparting suppleness to hair and preventing split ends or breakage of hair.

As Component (B), examples of the alkyl group in the dialkyl ethers and ethylene glycol dialkyl ethers with an alkyl group having from 18 to 22 carbon atoms include stearyl and behenyl groups. Examples of the acyl group in the ethylene glycol monofatty acid esters, ethylene glycol difatty acid esters, fatty acid monoethanolamides and acylated β-alanines with an acyl group having from 18 to 22 carbon atoms include a stearoyl group. Of these, ethylene glycol monofatty acid esters or ethylene glycol difatty acid esters each of which has, in its fatty acid composition, from 65 to 90 wt. % of stearic acid, and distearyl ether are preferred as Component (B) from the viewpoint of stability at low pH. They have preferably a pH of 4 or less at 25° C. when diluted to 20 times the weight with water, with a pH of 3.5 or less being more preferred.

As Component (B), two or more compounds may be used in combination. Its content may be from 0.05 to 10 wt. %, preferably from 0.1 to 5 wt. %, more preferably from 0.5 to 1 wt. % in the hair cosmetic composition of the present invention in order not only to impart the composition with a pearlescent gloss but also to heighten dispersion stability of Components (A) and (B) themselves and promote adsorption of them to hair.

A weight ratio of the content of Component (A) to the content of Component (B) preferably falls within the following range: (A):(B)=from 5:1 to 1:1000, more preferably from 1:2 to 1:30, still more preferably from 1:3 to 1:6 for improving the dispersion stability.

The hair cosmetic composition of the present invention may contain, as a cleansing base, another surfactant, preferably an amphoteric surfactant, anionic surfactant or nonionic surfactant with a view to stabilizing the hair cosmetic composition, improving feeling upon use, regulating viscosity, and solubilizing, dispersing or emulsifying each base.

Examples of the anionic surfactant include alkyl (or alkenyl) sulfates, polyoxyalkylene alkyl (or alkenyl) ether sulfates, alkane sulfonates, olefin sulfonates, alkylbenzene sulfonates, alkyl (or alkenyl) sulfosuccinates, dialkyl (or dialkenyl) sulfosuccinates, polyoxyalkylene alkyl (or alkenyl) sulfosuccinates, alkyl (or alkenyl) ether carboxylates, polyoxyalkylene alkyl (or alkenyl) ether carboxylates, polyoxyalkylene alkyl (or alkenyl) ether phosphates, fatty acid salts, N-acyl glutamates, N-acyl taurates, and N-acylmethyltaurine. Of these, polyoxyethylene alkyl ether sulfates, polyoxyethylene alkenyl ether sulfates and alkyl sulfates are preferred, with those represented by the below-described formula (5) or (6) being more preferred.

$$R^{14}O(CH_2CH_2O)_aSO_3M \quad (5)$$

$$R^{15}OSO_3M \quad (6)$$

(wherein, $R^{14}$ represents an alkyl or alkenyl group having from 10 to 18 carbon atoms, $R^{15}$ represents an alkyl group having from 10 to 18 carbon atoms, M represents an alkali metal, alkaline earth metal, ammonium, alkanolamine or basic amino acid, and a stands for a weight average number of 1 to 5).

Examples of the nonionic surfactant include polyoxyalkylene sorbitan fatty acid esters, polyoxyalkylene sorbitol fatty acid esters, polyoxyalkylene glycerin fatty acid esters, polyoxyalkylene fatty acid esters, polyoxyalkylene alkyl ethers, polyoxyalkylene alkylphenyl ethers, polyoxyalkylene (hydrogenated) castor oils, sucrose fatty acid esters, polyglycerin alkyl ethers, polyglycerin fatty acid esters, fatty acid alkanolamides, and alkyl glycosides. Of these, alkyl glycosides, polyoxyalkylene ($C_8$ to $C_{22}$) fatty acid esters, polyoxyethylene sorbitan fatty acid esters, polyoxyethylene hydrogenated castor oils and fatty acid alkanolamides are preferred. As the fatty acid alkanolamides, those with an acyl group having from 8 to 18, suitably from 10 to 16 carbon atoms, are preferred. As the fatty acid alkanolamides, either one of monoalkanolamides or dialkanolamides may be used, with those having a hydroxyalkyl group having from 2 to 3 carbon atoms being preferred. Examples thereof include oleic diethanolamide, palm kernel fatty acid diethanolamide, coconut oil fatty acid diethanolamide, lauric acid diethanolamide, polyoxyethylene coconut oil fatty acid monoethanolamide, coconut oil fatty acid monoethanolamide, lauric acid isopropanolamide and lauric acid monoethanolamide.

As the amphoteric surfactant, betaine surfactants may be used. Of these, betaine surfactants such as alkyldimethylaminoacetic acid betaines and fatty acid amidopropyl betaines are preferred. Of these, fatty acid amidopropyl betaines are preferred. As the fatty acid amidopropyl betaines, those with an acyl group having from 8 to 18, especially from 10 to 16 carbon atoms are preferred, with laurylamidopropyl betaine, palm kernelamidopropyl betaine and cocamidopropyl betaine being more preferred.

Two or more of these surfactants may be used in combination. Their total content in the whole composition is preferably from 1 to 30 wt. %, more preferably from 1 to 20 wt. %, still more preferably from 1 to 10 wt. % from the viewpoints of beautiful pearlescent gloss and dispersion stability. The content of each of the anionic surfactant, amphoteric surfactant and nonionic surfactant is preferably from 0 to 30 wt. %, more preferably from 1 to 30 wt. %, still more preferably from 2 to 20 wt. % within the above-described total content range.

The hair cosmetic composition of the present invention may further contain a cationic polymer in consideration of the texture of foam, lubricated feeling of foam, reduction in the friction between hair strands upon treatment and smoothness after drying. Examples of the cationic polymer include cationic cellulose derivatives, cationic starch, cationic guar gum derivatives, homopolymers of a diallyl quaternary ammonium salt, diallyl quaternary ammonium salt/acrylamide copolymers, quaternized polyvinylpyrrolidone derivatives, polyglycol-polyamine condensates, vinylimidazolium trichloride/vinylpyrrolidone copolymers, hydroxyethyl cellulose/dimethyldiallyl ammonium chloride copolymers, vinylpyrrolidone/quaternized dimethylaminoethyl methacrylate copolymers, polyvinylpyrrolidone/alkylamino acrylate copolymers, polyvinylpyrrolidone/alkylaminoacrylate/vinyl caprolactam copolymers, vinylpyrrolidone/methacrylamidopropyl trimethylammonium chloride copolymers, alkylacrylamide/acrylate/alkylaminoalkyl acrylamide/polyethylene glycol methacrylate copolymers, adipic acid/dimethylaminohydroxypropylethylenetriamine copolymers (CALTALETINE manufactured by US Sandos Corp.), and cationic polymers described in Japanese Patent Laid-Open No. Sho 53-139734 or Japanese Patent Laid-Open No. Sho 60-36407. Of these, cationic cellulose derivatives and cationic guar gum derivatives are preferred.

Two or more of these cationic polymers may be used in combination. Its content in the hair cosmetic composition of the present invention is preferably from 0.02 to 5 wt. %, more preferably from 0.05 to 1 wt. %, and even more preferably from 0.1 to 0.3 wt. % from the viewpoints of improvement in the foam quality upon treatment, manageability of hair after drying and improvement in feel. A ratio of the content of Component (A) to the content of the cationic polymer preferably falls within a range of from 50:1 to 1:100, more preferably from 10:1 to 1:10, still more preferably from 3:1 to 1:2 from the viewpoint of the adsorption of Components (A) and (B) to the hair.

The hair cosmetic composition of the present invention may further contain a conditioning component such as silicone in order to improve the finish after drying. Examples of the silicone include dimethylpolysiloxane, methylphenylpolysiloxane, amino-modified silicone, polyether-modified silicone, epoxy-modified silicone, fluorine-modified silicone, cyclic silicones, alkyl-modified silicones, and oxazoline-modified silicone. Of these, dimethylpolysiloxane, methylphenylpolysiloxane, amino-modified silicone, polyether-modified silicone, oxazoline-modified silicone and cyclic silicones are preferred. Two or more of these silicones may be used in combination. The content of the conditioning component preferably ranges from 0.01 to 20 wt. %, more preferably from 0.05 to 10 wt. %, still more preferably from 0.1 to 5 wt. % in the hair cosmetic composition of the present invention.

The hair cosmetic composition of the present invention may contain, in addition to the above-described components, water soluble polymers such as hydroxypropylmethyl cellulose, hydroxyl cellulose, polyvinyl alcohol, and polyethylene glycol; polyhydric alcohols such as sorbitol; humectants; chelating agents such as ethylene diamine tetraacetic acid (EDTA); drugs such as vitamin preparations; amino acids and derivatives thereof; fine particles of a polymer such as polyethylene, polystyrene, polymethyl methacrylate, nylon or silicone, and hydrophobic products thereof; extracts derived from animals or plants; ultraviolet absorbers; pearling agents; antiseptics; bactericides; pH regulators; colorants; and fragrances, according to purpose of use.

The hair cosmetic composition of the present invention preferably has a pH of from 1 to 5, more preferably a pH of from 2 to 4, still more preferably a pH of from 3 to 4 when applied to hair (diluted to 20 times the weight with water, 25° C.) in view of causing Component (A) (amphipathic amide lipid) to penetrate into hair sufficiently while suppressing stimulation. Organic acids or inorganic acids are used for regulation of the pH. Examples of the organic acid include hydroxy acids, monocarboxylic acids, dicarboxylic acids, and tricarboxylic acids. Hydroxy acids include glycolic acid, lactic acid, oxybutyric acid, malic acid and tartaric acid; monocarboxylic acids include acetic acid; dicarboxylic acids include malonic acid and succinic acid; and tricarboxylic acids include citric acid. Examples of the inorganic acids include hydrochloric acid and phosphoric acid. Of these, organic acids are preferred, with α-hydroxycarboxylic acids being preferred and lactic acid and malic acid being more preferred.

The hair cosmetic composition of the present invention may be provided in any form selected from liquid, powder, gel and granule as needed. A liquid composition using water or a lower alcohol as a solvent is preferred, with a liquid composition using water being especially preferred.

The hair cosmetic composition of the present invention is preferably used in bath rooms as a shampoo composition, rinse-in-shampoo, treatment or conditioner, more preferably a shampoo composition.

The hair cosmetic composition of the present invention can be prepared in a conventional manner. Described specifically, it is available by mixing water, a surfactant if necessary, and another optional component, with components (A) and (B), heating the resulting mixture at a melting point of Components (A) and (B) or greater, stirring and then gradually cooling while stirring, keeping the temperature of the reaction mixture at room temperature to precipitate Component (B). Alternatively, Component (B) which has been prepared separately by melting and cooling in an aqueous medium may be added to a mixture of the other components.

By treating hair with the hair cosmetic composition of the present invention, it is possible to protect hair from physical and chemical stimulations and thereby prevent spilt ends or broken hair, and impart hair with natural smoothness, moist feeling, resilience and strength and moisture retention property. The hair cosmetic composition of the present invention may be washed away after being applied to hair.

EXAMPLES

The present invention will be described more specifically by Examples. It should however be borne in mind that the present invention is not limited to or by them.

In the below-described Examples and Comparative Examples, the pH is a value measured (by a pH meter) at 25° C. when the composition is diluted with water to 20 times the weight. The amphipathic amide lipid employed in Examples is either one of the following compounds.

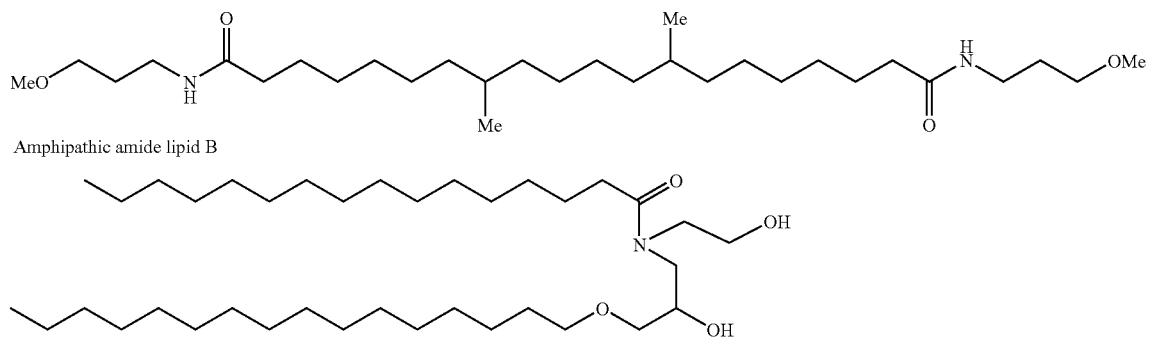

Examples 1 to 3, and Comparative Examples 1 to 2

Compositions shown in Table 1 were prepared and "resilience and strength", "smoothness", and "moist feeling" of the hair after treatment and "storage stability" of each composition were evaluated.

(Organoleptic Evaluation)

After the hair was wet sufficiently, it was shampooed with 5 g or 10 g of a shampoo composition (5 g for semi-long hair, and 10 g for long hair). The hair was rinsed well and then, dried enough with hot air from a dryer. Evaluation of the shampoo was made by a panel of 5 Experts by the average score obtained in accordance with the below-described criteria.

Evaluation Criteria:

(1) Resilience and Strength of the Hair after Drying
    4: A marked improvement in resilience and strength is observed.
    3. An improvement in resilience and strength is observed.
    2: A slight improvement in resilience and strength is observed.
    1: Neither resilience nor strength is improved.
    0: Resilience and strength are lost.

(2) Smoothness of the Hair after Drying
    4: A marked improvement in smoothness is observed.
    3: An improvement in smoothness is observed.
    2: A slight improvement in smoothness is observed.
    1: No improvement in smoothness is observed.
    0: A deterioration in smoothness is observed.

(3) Moist Feeling of the Hair after Drying
    4: A marked improvement in moist feeling is observed.
    3: An improvement in moist feeling is observed.
    2: A slight improvement in moist feeling is observed.
    1: No improvement in moist feeling is observed.
    0: Moist feeling is lost.

(Storage Stability)

The composition was stored in a clear glass container (100 mL) at 50° C. for 1 month and the change in appearance was observed.
    A: No change
    B: A slight change
    C: Separation or gelation occurred.

Example 4

Conditioning Shampoo

| | (wt. %) |
|---|---|
| Sodium polyoxyethylene (2) lauryl ether sulfate | 8.0 |
| Sodium lauryl sulfate | 5.0 |
| Cationic guar gum | 0.5 |
| Amphipathic amide lipid A | 2.0 |
| Trisodium citrate | 1.0 |
| Lauroyl amidopropylbetaine | 3.0 |
| Cocoyl monoethanolamide | 0.7 |
| Dimethicone (viscosity: 100000 mPa·s) | 0.5 |
| Amodimethicone (product of Dow Corning Toray Silicone "SM8704C") | 0.1 |
| Myristyl alcohol | 1.0 |
| Ethylene glycol distearate | 3.0 |
| Polypropylene glycol (Mw = 400) | 0.5 |
| Glycerin | 1.0 |
| Maleic acid | Amount enough for pH adjustment |
| Deionized water | Balance |

The above-described shampoo (pH 3.7) can impart good smoothness and moist feeling to the hair after shampooing and inhibit the appearance of split ends or broken hair.

Example 5

Conditioning Shampoo

| | (wt. %) |
|---|---|
| Sodium polyoxyethylene (2) lauryl ether sulfate | 11.0 |
| Sodium lauryl sulfate | 5.0 |
| Cationic guar gum | 0.3 |
| Amphipathic amide lipid B | 2.0 |
| Malic acid | 0.75 |
| Lactic acid | 0.1 |

TABLE 1

(Unit of content is wt. %)

| | | Examples | | | Comparative Examples | |
|---|---|---|---|---|---|---|
| | | 1 | 2 | 3 | 1 | 2 |
| (A) | Amphipathic amide lipid A | 0.5 | — | 0.5 | — | — |
| | Amphipathic amide lipid B | — | 0.1 | — | 2 | — |
| (B) | Ethylene glycol distearate | 2 | — | — | — | 1 |
| | Distearyl ether | — | 2 | 2 | — | — |
| Others | Sodium polyoxyethylene (2) lauryl ether sulfate | 10 | 10 | 10 | 10 | 10 |
| | Sodium lauryl sulfate | 5 | 5 | 5 | 5 | 5 |
| | Cocoyl monoethanolamide | 0.5 | 0.5 | 0.5 | 0.5 | 0.5 |
| | Cationic hydroxyethylcellulose | 0.3 | 0.3 | 0.3 | 0.3 | 0.3 |
| | Cationic guar gum | 0.5 | 0.5 | 0.5 | 0.5 | 0.5 |
| | 50 wt. % aq. NaOH soln/50 wt. % citric acid | q.s.* | q.s.* | q.s.* | q.s.* | q.s.* |
| | Purified water | Balance | Balance | Balance | Balance | Balance |
| | pH | 3.5 | 3.5 | 3 | 3.5 | 3.5 |
| | Buffering capacity (NaOH-gram equivalent/L) | 0.02 | 0.01 | 0.01 | 0.01 | 0.01 |
| Evaluation | Resilience and strength of hair | 3.1 | 2.7 | 3.9 | 1.8 | 1.6 |
| | Smoothness of hair | 3.8 | 3.6 | 3.8 | 2.1 | 1.2 |
| | Moist feeling of hair | 3.8 | 3.7 | 3.8 | 2.2 | 1.0 |
| | Storage stability (50° C. × 1 month) | A | A | A | C | A |

*amount enough for pH adjustment

-continued

| | (wt. %) |
|---|---|
| Sodium chloride | 0.2 |
| Benzyl alcohol | 0.5 |
| Cocoyl monoethanolamide | 1.0 |
| Amodimethicone (product of Dow Corning Toray Silicone "SM8704C") | 0.1 |
| Myristyl alcohol | 1.0 |
| Cetanol | 0.5 |
| Ethylene glycol distearate | 2.0 |
| Cationic hydroxyethylcellulose | 0.3 |
| Glycerin | 1.0 |
| Sodium hydroxide | Amount enough for pH adjustment |
| Deionized water | Balance |

The above-described shampoo (pH 3.7) can impart good smoothness and moist feeling to the hair after shampooing and inhibit the appearance of split ends or broken hair.

Example 6

Conditioning Shampoo

| | (wt. %) |
|---|---|
| Sodium polyoxyethylene (2) lauryl ether sulfate | 8.0 |
| Cationic guar gum | 0.3 |
| Amphipathic amide lipid B | 2.0 |
| Malic acid | 0.5 |
| Lactic acid | 0.5 |
| Sodium chloride | 1.0 |
| Lauroyl amidopropylbetaine | 3.0 |
| Dimethicone (viscosity: 100000 mPa · s) | 0.5 |
| Amodimethicone (product of Dow Corning Toray Silicone "SM8704C") | 0.1 |
| Myristyl alcohol | 1.0 |
| Cetanol | 0.5 |
| Behenyltrimonium chloride | 0.5 |
| Ethylene glycol distearate | 2.0 |
| Benzyloxyethanol | 0.5 |
| Sodium hydroxide | Amount to adjust pH |
| Deionized water | Balance |

The above-described shampoo (pH 3.7) can impart good smoothness and moist feeling to the hair after shampooing and inhibit the appearance of split ends or broken hair.

Example 7

Antidandruff Shampoo

| | (wt. %) |
|---|---|
| Sodium polyoxyethylene (2) lauryl ether sulfate | 10.0 |
| Sodium lauryl sulfate | 5.5 |
| Cationic guar gum | 0.3 |
| Amphipathic amide lipid A | 2.0 |
| Malic acid | 1.0 |
| Sodium chloride | 0.2 |
| Benzyloxyethanol | 0.5 |
| Cocoyl monoethanolamide | 0.5 |
| Dimethicone (viscosity: 100000 mPa · s) | 0.5 |
| Amodimethicone (product of Dow Corning Toray Silicone "SM8704C") | 0.1 |
| Myristyl alcohol | 1.0 |

-continued

| | (wt. %) |
|---|---|
| Cetanol | 0.5 |
| Ethylene glycol distearate | 3.0 |
| Cocoyl benzalkonium chloride | 0.5 |
| Cationic hydroxyethylcellulose | 0.3 |
| Glycerin | 1.0 |
| Sodium hydroxide | Amount enough for pH adjustment |
| Deionized water | Balance |

The above-described shampoo (pH 3.7) can impart good smoothness and moist feeling to the hair after shampooing and inhibit the appearance of split ends or broken hair.

Example 8

Hair Conditioner

| | (wt. %) |
|---|---|
| Stearyl trimethylammonium chloride | 3.0 |
| Behenyl alcohol | 8.0 |
| Dipropylene glycol | 5.0 |
| Concentrated glycerin | 5.0 |
| Polypropylene glycol | 2.5 |
| Amphipathic amide lipid A | 0.5 |
| Dimethicone-containing emulsion (product of Dow Corning Toray Silicone, "CF-2450") | 2.0 |
| Malic acid (50 wt. %) | 1.0 |
| Lactic acid (90 wt. %) | 1.7 |
| Sunflower oil | 0.5 |
| Benzyloxyethanol | 1.0 |
| Dipentaerythritol fatty acid ester | 0.1 |
| Ethylene glycol distearate | 2.0 |
| Phenoxyethanol | 0.1 |
| Deionized water | Balance |

The above-described conditioner (pH 3.1) is excellent in smoothness upon rinsing, and smoothness and moist feeling after drying, and also is excellent in stability.

Example 9

Hair Treatment

| | (wt. %) |
|---|---|
| N,N-Dimethyloctadecyloxypropylamine | 6.0 |
| Behenyl alcohol | 15.0 |
| Dipropylene glycol | 5.0 |
| Concentrated glycerin | 5.0 |
| Polypropylene glycol | 2.5 |
| Amphipathic amide lipid A | 0.5 |
| Dimethicone-containing emulsion (product of Dow Corning Toray Silicone, "CF-2460") | 2.5 |
| Aminoethylaminopropyl methylpolysiloxane copolymer | 0.2 |
| Malic acid (50 wt. %) | Amount enough for pH adjustment |
| Lactic acid (90 wt. %) | 2.2 |
| Sunflower oil | 1.5 |
| Benzyloxyethanol | 1.0 |
| Dipentaerythritol fatty acid ester | 0.2 |
| Oleic acid | 0.1 |
| Ethylene glycol distearate | 2.0 |

-continued

| | (wt. %) |
|---|---|
| Phenoxy ethanol | 0.5 |
| Coconut oil fatty acid | 0.1 |
| Deionized water | Balance |

The above-described hair treatment (pH 3.7) is excellent in smoothness upon rinsing and smoothness and moist feeling after drying and is also excellent in stability.

The invention claimed is:

1. A hair cosmetic composition comprising the following components (A) and (B):

(A): from 0.1 to 5 wt. % of an amphipathic amide lipid, selected from the group consisting of Amphipathic amide lipid A

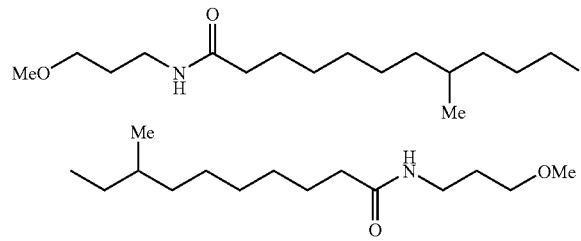

Amphipathic amide lipid B

and (B): from 0.1 to 5 wt. % of ethylene glycol distearate and
(C): 0.02 to 5 wt % of cationic polymer selected from the group consisting of cationic hydroxyethyl cellulose and cationic guar gum and further comprising a surfactant in an amount of 1 to 30 wt %
wherein a ratio of components (A):(B) ranges from 1:2 to 1:30.

2. The hair cosmetic composition of claim 1, having a pH of from 1 to 5 at 25° C. when diluted to 20 times its weight with water.

3. The hair cosmetic composition of claim 1, wherein component (A) is present in a an amount of 0.5 to 1 wt. %.

4. The hair cosmetic composition of claim 1, wherein component (B) is present in an amount of 0.5 to 1 wt. %.

5. The hair cosmetic composition of claim 1, wherein a ratio of components (A):(B) ranges from 1:3 to 1:6.

6. The hair cosmetic composition of claim 1, wherein component (A) and said cationic polymer are present in a ratio of 3:1 to 1:2.

7. The hair cosmetic composition of claim 1, wherein a ratio of components (A):(B) ranges from 1:1 to 1:20.

* * * * *